United States Patent [19]

Winkler et al.

[11] Patent Number: 5,527,348

[45] Date of Patent: Jun. 18, 1996

[54] MAGNETICALLY PERMEABLE E-SHIELD AND METHOD OF CONNECTION THERETO

[75] Inventors: Thomas J. Winkler, Isanti; John J. Grevious, Minneapolis; Mark W. Sandberg; Ray W. Gravlin, both of Coon Rapids, all of Minn.

[73] Assignee: Medtronic, Inc., Minneapolis, Minn.

[21] Appl. No.: 383,041

[22] Filed: Feb. 3, 1995

[51] Int. Cl.⁶ .................................................. A61N 1/37
[52] U.S. Cl. .............................................................. 607/30
[58] Field of Search ........................... 607/1, 9, 30, 31, 607/32, 33, 38, 59, 60, 154, 155

[56] References Cited

U.S. PATENT DOCUMENTS

| 4,068,292 | 1/1978 | Berry et al. | 607/155 |
| 4,071,032 | 1/1978 | Schulman | 607/33 |
| 5,345,362 | 9/1994 | Winkler | 361/681 |

OTHER PUBLICATIONS

*Medtronic 9760 Instruction Manual* Programmer: This manual covers the use of 9855E Software, Medtronic, Inc., Apr. 1990.

*Primary Examiner*—William E. Kamm
*Attorney, Agent, or Firm*—Harold R. Patton; Reed A. Duthler

[57] ABSTRACT

A method and apparatus for providing electrical field (E-field) shielding for electro-magnetic devices. In one embodiment of the invention, a programming head from an implantable medical device programming system is housed within a nonconductive exoskeleton. The programming head contains an antenna that is preferably shielded from E-fields but not from magnetic fields (H-fields). A pattern of electrically conductive material, such as a nickel-acrylic paint or the like, is applied to interior surfaces of the exoskeleton, such that at least two (preferably four) distinct and discontinuous areas of conductive material are defined thereon. A collar for providing strain relief for a programming head cable entering through an aperture in the exoskeleton is maintained in electrical contact with each area of conductive material in said exoskeleton. The collar is preferably made of conductive material, and is also coupled to at least one conductor in the programming head cable, such that the conductive areas are coupled to ground via the cable. In other embodiments, both E-shielding and H-shielding may be similarly accomplished by coating the entire inner surface of the exoskeleton.

15 Claims, 4 Drawing Sheets

MAGNETICALLY PERMEABLE E-SHIELD AND METHOD OF CONNECTION THERETO

FIELD OF THE INVENTION

This invention relates generally to the field of electromagnetic systems, and more particularly relates to a method and apparatus for providing magnetically-permeable electric field shielding in electro-magnetic systems.

BACKGROUND OF THE INVENTION

Communications systems employing radio-frequency (RF) transmitters and receivers are very common and well-known. One application of such communication systems is in the field of automatic, body-implantable medical devices, such as pacemakers, defibrillators, neural stimulators, and the like. RF communication is used to establish "downlink" telemetry channels, in which operational data and commands are transmitted from an external programming unit transmitter to a receiver in an implanted device, and to establish "uplink" telemetry channels, in which information is transmitted from the implanted device's transmitter to a receiver in the external unit.

A specific example of a telemetry system for body-implantable medical devices is the Medtronic Model 9790 Programmer, commercially available from the assignee of the present invention. The Model 9790 Programmer, with appropriate software modules, can be used to communicate (both uplink and downlink) with numerous body-implantable devices manufactured by Medtronic, Inc.

In the prior art, as typified by the Model 9790 Programmer in conjunction with a Medtronic implantable pacemaker, for example, an antenna in the form of a multiple-turn wire coil is disposed within the hermetic enclosure of the implanted device. Downlink RF signals transmitted to the implanted device induce a current in the coil antenna, and this current is amplified and applied to a receiver input for demodulation and extraction of the information content of the RF signal. Similarly, for uplink communication, electrical currents applied directly to the implanted coil antenna cause RF electromagnetic signals-to be generated, such that these signals can be received by a corresponding antenna associated with the external unit.

For various reasons, including the desire to minimize the necessary strength of both uplink and downlink telemetry signals in implantable device systems, the external unit of an implantable device system typically includes a relatively small, handheld programming head containing the external antenna, so that this programming head can be placed directly over the implant site of the implanted device, thus minimizing the distance between the implanted and external antennas. The head is typically connected to the larger base unit of the programmer via a multiple-conductor cable. The aforementioned Model 9790 is one example of a implantable device programmer having this configuration. The Model 9790 is described in further detail in co-pending U.S. Pat. No. 5,345,362 to Winkler, entitled "Portable Computer Apparatus With Articulating Display Panel." The Winkler '362 patent is hereby incorporated by reference herein in its entirety.

As will be appreciated by those of ordinary skill in the art, an important principle underlying RF communication systems is that time-varying electric fields ("E-fields") produce magnetic fields ("H-fields"), while time-varying magnetic fields produce electric fields. Those of ordinary skill in the art will also appreciate that RF signals such as are transmitted and received in RF communication systems have two components: an electric field component and a magnetic field component. The E-field and H-field components of an RF signal are interrelated but distinct (as expressed by Maxwell's equations).

In many communication system applications, including typical telemetry circuits for implantable medical device systems, it is the H-field component that is of interest, rather than the E-field component, since it is the time-varying H-field component of an RF signal which is capable of inducing a current in a coil antenna (i.e., which is capable of being "received"). As a result, the E-field component of RF communication signals in many cases is regarded as "noise" to be ignored. Accordingly, telemetry systems are often provided with shielding which attenuates or shields E-fields, but which is permeable to H-fields.

Magnetic-permeable E-shields can be implemented in a number of ways. One common implementation involves surrounding components to be protected from unwanted E-fields with a metallic shroud or cage. Magnetic permeability is realized by ensuring that the metallic enclosure is "broken" or non-continuous (i.e., it must have gaps), so that it does not provide a short-circuit for impinging H-fields and thus shield both E-fields and H-fields.

Although a discontinuous metallic shroud in electromagnetic equipment is a fairly straightforward and effective E-shield, there are several potential difficulties with such an arrangement in practical implementation, particularly in application in programming heads for implantable medical devices. One such difficulty arises simply from the fact that one or more extra mechanical components—the metallic shroud itself—are required. ( Usually, because the shield must be discontinuous, the shield comprises at least two parts.) This requirement increases the complexity of the design and assembly, and perhaps the size of the device. Additionally, the need to electrically couple the metallic shield to a ground terminal in the programming head, and ultimately to a ground conductor in the cable connecting the head to the programmer base unit, increases the amount of hardware necessary, increases the complexity of the design and assembly of the device, and increases the risk of electrical or mechanical failure of the programming head, e.g., due to mishandling, dropping, age, etc. ...

A further difficulty in providing a metallic E-shield is that it is typically desirable to dispose E-shielding as physically far from the antenna as possible, to avoid capacitive coupling of the shield and antenna.

SUMMARY OF THE INVENTION

In view of the foregoing considerations, it is believed to be desirable to provide an improved method and apparatus for magnetically-permeable E-shielding of electro-magnetic systems like medical device programming heads.

In accordance with one embodiment of the invention, magnetic-permeable E-shielding for the programming head of an implantable device programming system is accomplished by coating the inside surfaces of the programming head's enclosure with a conductive paint, applied in a pattern that results in multiple discontinous areas of conductive material. The conductive material functions to shield E-fields, while the discontinuity of the pattern allows for H-field permeability.

In accordance with another aspect of the invention, establishing the necessary electrical contact between the conductive E-shielding applied to the inner surfaces of the programming head's enclosure and a ground terminal external to the programming head (i.e., in the programmer base unit) is accomplished by providing a conductive element which is in contact with each of the conductive E-shield areas and which passes through the programming head's enclosure to be coupled with a ground conductor external to the programming head.

In one embodiment, the conductive element for contacting the conductive E-shield areas is a strain-relief collar for the programming head cable which couples the programming head to the programming base unit. The strain-relief collar is preferably made of a conductive polymer or the like, engaged in a suitable notch or hole in the programming head's enclosure so that a flared portion of the collar that is within the programming head's enclosure is maintained in firm contact with the inner surfaces of the enclosure and thus with the conductive E-shield areas painted onto the inner surface of the enclosure.

Among the advantages that the present invention is believed to offer are: a reduction in the number of physical components of the programming head, and hence decreased size, and complexity of design and assembly of the programming head; increased reliability of the contact between the E-shield and a ground terminal external to the programming head; and a maximization of the distance between the programming head's antenna and the E-shielding, leading to a minimization of capacitive coupling between the antenna and the E-shielding.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1:
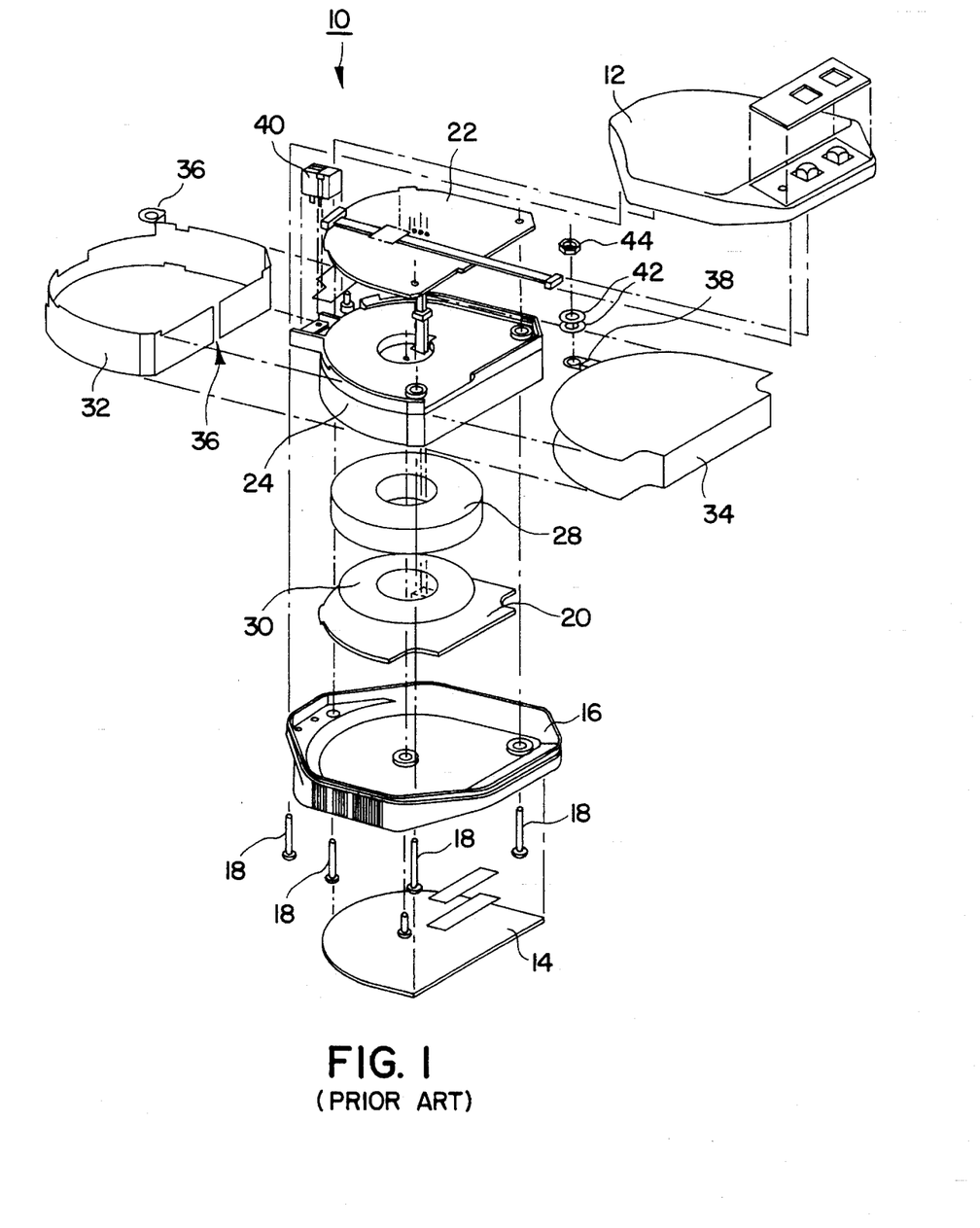
FIG. 1 is an exploded view of a prior art programming head for an implantable medical device programming system.

Referring to FIG. 1, there is shown an exploded view of a prior art programming head 10. The case assembly or "exoskeleton" of programming head 10, which is typically made of plastic, (PVC, ABS, or the like,) comprises top, and bottom with side portions 12, and 16, respectively, held together with a plurality of screws 18. Within the case assembly are first and second printed circuit boards 20 and 22 containing the operational circuitry of the programming head. Printed circuit boards 20 or 22 also have a wire-coil antenna (not shown in FIG. 1) embedded therein. Printed circuit boards 20 and 22 are mounted on a rigid retainer 24 which is also preferably made of plastic. Sandwiched between printed circuit boards 20 and 22 within retainer 24 is a large permanent magnet 28 for effectuating closure of a reed switch in an implanted device when programming head 10 is placed over the implant site, in accordance with common practice in the art. An insulating shim 30 may be provided to insulate magnet 28 from printed circuit board 20.

With continued reference to FIG. 1, a magnetically-permeable E-shield in programming head is implemented with two metallic components 32 and 34 which surround retainer 24 on substantially all sides thereof. In particular, metal shield portion 32 extends around all sides of retainer 24 and boards 20 and 22, except for a small discontinuity or gap 36 provided, as noted above, to ensure magnetic permeability of the shield. Metal shield portion 34 extends above and below retainer 24.

To effectuate coupling of metallic shields portions 32 and 34 to electrical ground, both shield components 32 and 34 are provided with extending tabs 36 and 38, respectively, which are aligned with one another when programming head 10 is assembled. When programming head is assembled, tabs 36 and 38 are held in electrical contact with a ground terminal of a cable connector 40 by means of washers 42 and a nut 44. A programming head cable (not shown) extends from cable connector 40 to the programmer base unit (not shown) to complete the connection between shield components 32 and 34 and ground.

From the foregoing description of a prior art E-shielding arrangement, it should be apparent that the complexity of design and assembly, the size, and the risk of electrical or mechanical failure of programming head 10 are all increased as a result of the need for numerous interconnected components.

Figure 2:
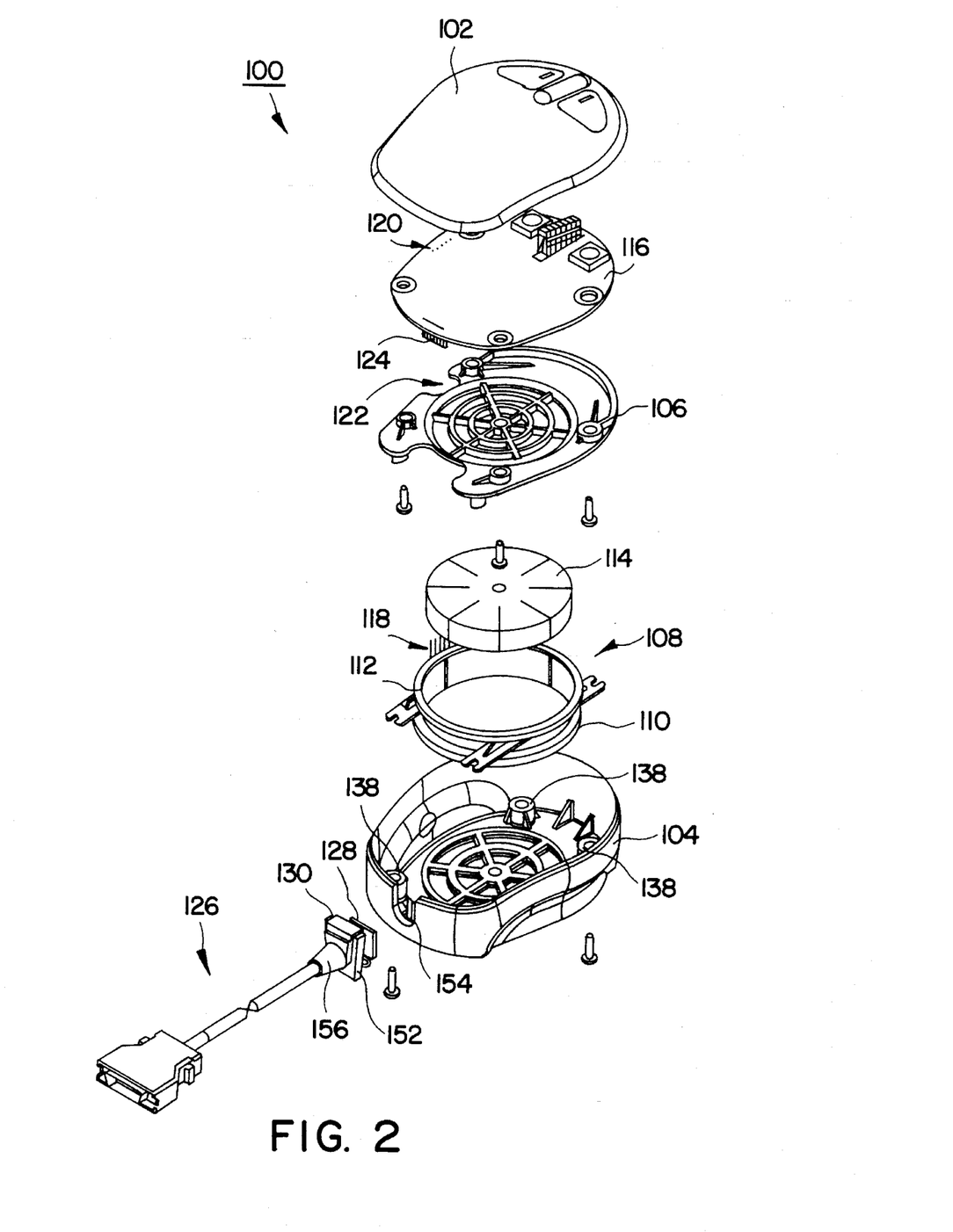
FIG. 2 is an exploded view of a programming head in accordance with one embodiment of the present invention.

Turning now to FIG. 2, on the other hand, a programming head 100 in accordance with one embodiment of the present invention is shown, wherein the magnetically-permeable E-shielding adds virtually no complexity, size, weight, or risk of failure. Programming head 100 includes an outer exoskeleton comprising top and bottom, portions 102 and 104, respectively, and an internal retainer element 106, each of which are preferably made of molded plastic, ABS, or the like. Housed within the exoskeleton is a wire coil antenna assembly 108 comprising one or more wires 110 coiled multiple times around a rigid spool 112. Disposed within spool 112 is a substantially disk-shaped permanent magnet 114 for effectuating reed-switch closure, as described above and in accordance with common practice in the art.

Also disposed within the exoskeleton of programming head 100, and disposed generally on top of retainer 106, is a printed circuit board assembly 116 having the operative electronic circuitry of programming head 100 disposed thereon. In accordance with one aspect of the disclosed embodiment, electrical connection between antenna assembly 108 and the circuitry on printed circuit board 116 is accomplished with rigid electrical connector pins which extend upward from spool 112 to be received in through-holes 120 disposed in printed circuit board 116. This arrangement is believed to be advantageous, since the need for less rigid wires or ribbon cable, which are more susceptible to breakage and fatigue and which can complicate the assembly process, is eliminated. A notch 122 is provided in retainer element 106 to allow passage of connector pins 118 through to printed circuit board 116.

A projecting electrical connector 124 is provided on printed circuit board 106 to effectuate connection between the electronic circuitry of programming head 100 and the conductors of a programming head cable assembly 126. In particular, connector 124 is received in a socket 128 extending out from a head connector assembly 130 on the programming head end of cable assembly 126. This pin-and-socket connection between cable assembly 126 and printed circuit board 124 reduces the complexity and fragility of other approaches, such as soldering wires or ribbon cable to circuit board 124.

In accordance with an important aspect of the present invention, magnetic-permeable E-shielding of programming head 100 is accomplished through the application of a pattern of conductive paint to inner surfaces of exoskeletal components 102 and 104. This is illustrated in more detail in FIGS. 3a and 3b, which show the inner surfaces of exoskeletal component 104, and FIGS. 4a and 4b, which show the inner surfaces of exoskeletal component 102.

Figure 3A:
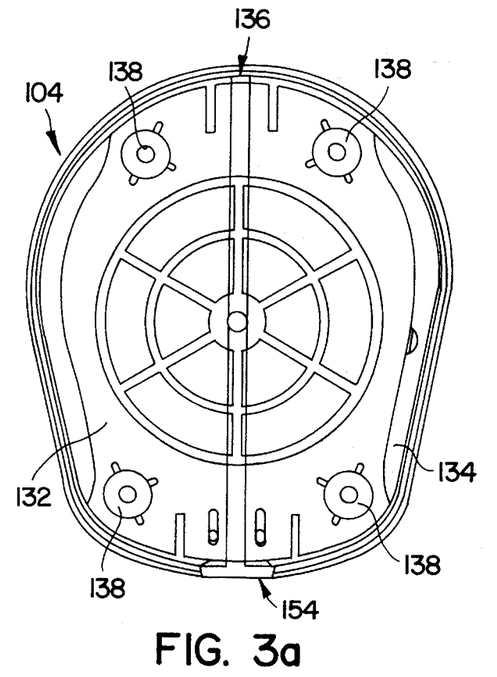
FIGS. 3a and 3b are top and side views, respectively, of a bottom portion of the exoskeleton of the programming head from FIG. 2.
Figure 3B:
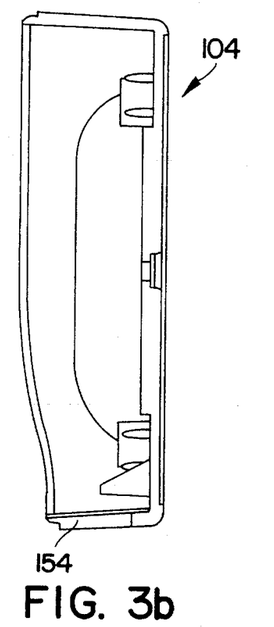

Referring to FIGS. 3a and 3b, the cross-hatched areas therein are areas that have been coated (painted) with a conductive material in accordance with the disclosed embodiment of the invention. In the presently preferred embodiment, the conductive material is a nickel acrylic spray, type R-65, commercially available from BEE Chemical Co., Inc., Lansing, Illinois, although it is believed that other types of conductive coatings may be found to be suitable for the purposes of practicing the present invention. As shown in FIGS. 3a and 3b, the nickel acrylic spray is applied to two symmetric, separate, and non-overlapping areas 132 and 134 of component 104 and isolation between top and bottom. Areas 132 and 134 are separated by a longitudinal gap 136 of substantially uniform width. Experimental data shows that a gap 136 of no more than 0.130-inches is preferable. FIG. 3b shows that the conductive coating is applied to the sides of component 104, although it is important that separation of areas 132 and 134 be maintained in order to avoid providing a short-circuit for magnetic fields, as previously described.

With continued reference to FIGS. 3a and 3b, it should be noted that four bosses 138 (which are also visible in FIG. 2) for receiving screws to hold programming head 100 together, are disposed on the inner surface of component 104. Being within areas 132 and 134, these bosses 138 are also preferably covered with the conductive coating.

Figure 4A:
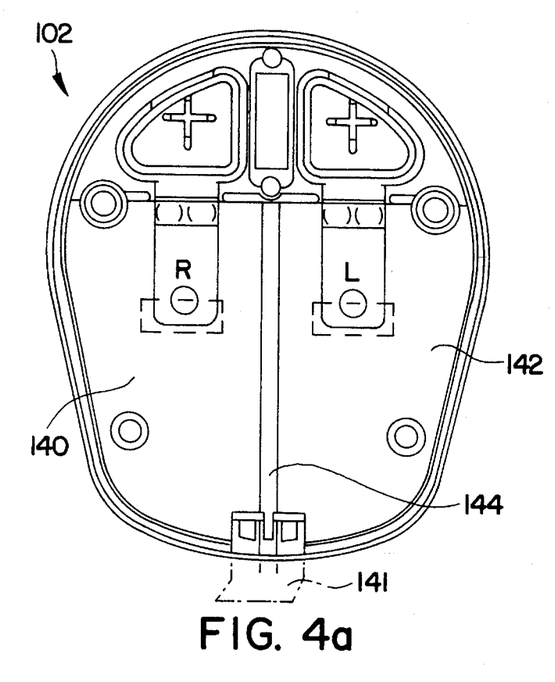
FIGS. 4a and 4b are top and side views, respectively, of a top portion of the exoskeleton of the programming head from FIG. 2.
Figure 4B:
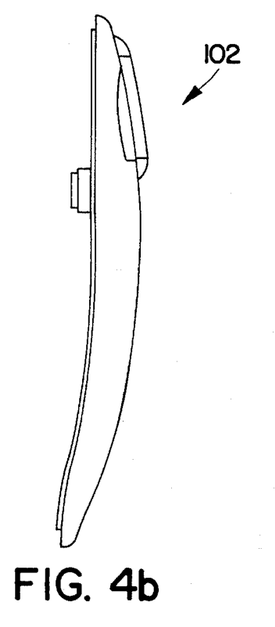

Turning now to FIGS. 4a and 4b, it can be seen that the nickel acrylic coating is also applied to the upper exoskeletal component 102, in cross-hatched areas 140 and 142. As with component 104, the conductive coating areas 140 and 142 on component 102 are separated by a 0.130-inch or so gap 144, such that no short-circuit for magnetic fields is created. Isolation is also maintained between the coated areas of components 102 and 104. A compressable conductive gasket 141 is employed to enhance the contact the upper case 102 and the strain relief 150.

Examination of FIGS. 3a, 3b, 4a, and 4b will reveal that four separate "quadrants" 132, 134, 140, and 142, of conductive coating are defined on the inner surface of the exoskeleton of programming head 100 to provide a magnetic-permeable E-shield which occupies virtually no space within the exoskeleton. The four quadrants of conductive material are mutually separated from one another, but are all within close range of one another at the point where programming head cable 126 enters the exoskeleton of programming head 100. Although this is the presently preferred configuration of conductive coating, it is contemplated that other patterns, in which perhaps more separate areas of conductive coating are defined, may also be suitable for the purposes of practicing the present invention.

As previously noted with reference to the prior art programming head 10 of FIG. 1, it is necessary to electrically couple the conductive components of an E-shield to electrical ground, as would be known to those of ordinary skill in the art. In prior art programming head 10, this coupling necessitated the use of washers 42 and nut 44 in cooperation with electrical connector 40. Such a configuration tends to increase the complexity of the assembly process for programming head 10, and increases the risk of failure of the shield system, e.g., if nut 40 were to become loosened over time.

Figure 5A:
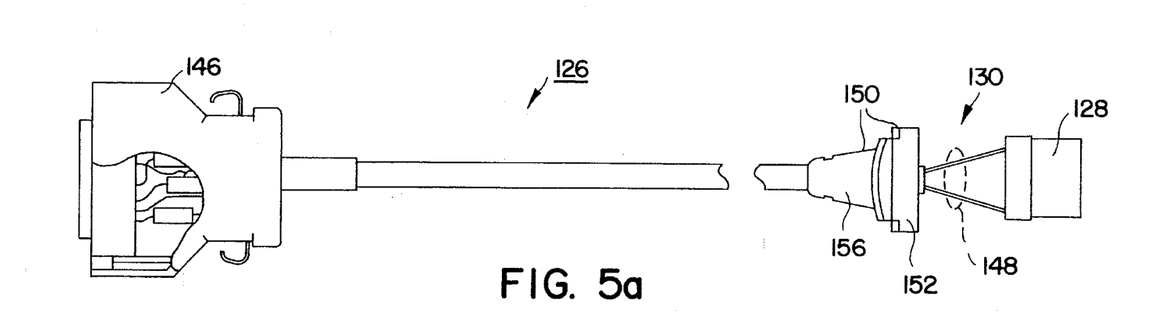
FIGS. 5a, 5b, and 5c are top and side views, respectively, of the programming head cable assembly from the programming head of FIG. 2.
Figure 5B:
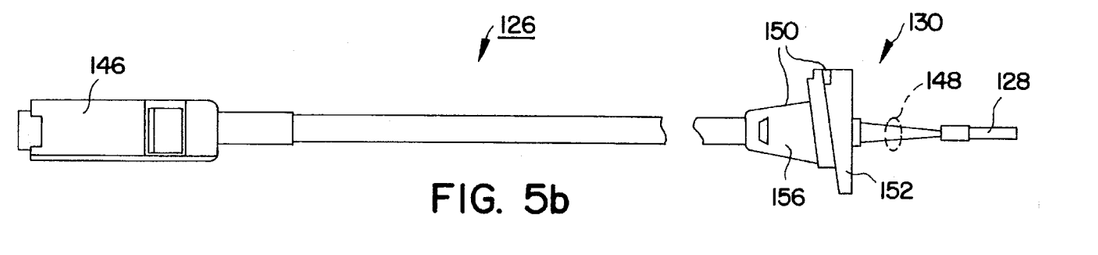
Figure 5C:
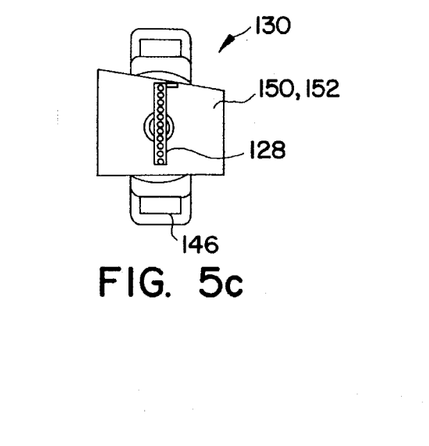

In order to overcome these potential limitations of the prior art, the electrical coupling of the conductive coatings 132, 134, 140 and 142 in programming head 100 of FIG. 2 is accomplished by head connector assembly 130 on the programming head end of programmer cable assembly 126, which is shown in more detail in FIGS. 5a, 5b, and 5c.

FIGS. 5a, 5b, and 5c are top, side, and programmer head end views, respectively, of programming head cable assembly 126 for programming head 100 of FIG. 2. As shown in those Figures, a conventional multi-pin connector 146, such as might be found on cables used in standard personal computer equipment and the like, is disposed on one end ("the programmer end") of cable assembly 126, while head connector assembly 130 is disposed on another end ("the programming head end") of cable assembly 126. A plurality of conductors within cable assembly 126, designated collectively as 148 in the Figures, extend through head connector assembly 130 and terminate at the programming head end of cable 126 at socket 128 which, as previously noted, is adapted to receive and establish electrical connection with a plurality of pins 124 disposed on printed circuit board 116 in programming head 100. This modular design is such that, during assembly of programming head 100, cable assembly 126 may be readily coupled to printed circuit board 116 by engaging socket 128 with pins 124.

Head connector assembly 130 further comprises a strain-relief collar element 150 which serves dual purposes of providing strain relief for cable 126 at the point of connection to the exoskeleton of programming head 100 and also effectuating the electrical coupling of conductive areas 132, 134, 140, and 142 to a ground conductor in cable 126, as will be hereinafter described in greater detail.

In accordance with one feature of the present invention, strain relief collar element 150 is a unitary element that is injection-molded onto the end of cable 126 and is made out of two different materials. A first material, preferably a conductive polymer, is used to form a flared portion 152 of strain-relief collar 150 which, upon assembly of programming head 100, is engaged inside the exoskeleton thereof behind a notch (designated with reference numeral 154 in FIGS. 2, 3a, and 3b) in exoskeletal component 104. In the presently preferred embodiment, the conductive material is commercially-available Electrafil No. TPE2140/EC copolyester elastomer with conductive carbon powder. Flared conductive portion 152 serves to prevent cable assembly 126 from being withdrawn from programming head 100 as in a conventional strain-relief collar. In addition, however, flared portion 152 is maintained in firm electrical contact with all four conductive areas applied to the inner surfaces of exoskeletal components 102 and 104, which areas converge, but do not come into contact with one another, at notch 154 where cable 126 enters the exoskeleton of programming head 100. During the molding of flared portion 152 onto the end of cable 126, one or more ground conductors in cable 126 are exposed (e.g., folded back) at the programming head end thereof, such that electrical contact is made between the ground conductor(s) and conductive flared portion 152 of strain-relief collar 150. Thus, conductive flared portion 152 effectively comprises a ground contact of cable 126 which is maintained in electrical contact with the E-shield coating of programming head 100. In this way, the ground conductors in cable 126 may be connected, at the programmer end thereof, to a ground terminal in the programming unit (not shown).

A second, non-conductive material (e.g., 90 durometer PVC) is molded adjacent to the strain-relief collar 150 which extends out of the exoskeleton of programming head 100. This non-conductive portion is represented by cross-hatched area 156 in FIGS. 5a and 5b, and can also be seen in FIG. 2. This non-conductive portion 156 ensures that no conductive part of strain-relief collar 150 may be inadvertently brought into contact with external objects, thereby violating safety requirements. The size and shape of non-conductive portion 156 is such that a portion thereof is received snugly within notch 154 in exoskeletal portion 104 of programing head 100.

Those of ordinary skill in the art will appreciate that the configuration of cable assembly 126 with a conductive portion maintained in firm electrical contact with the E-shielding of programming head 100 advantageously eliminates the hardware necessary to effect a connection to ground in prior art E-shielding arrangements, as typified by that shown in FIG. 1.

From the foregoing detailed description of a specific embodiment of the invention, it should be apparent that a method and apparatus for providing magnetic-permeable E-shielding in an electro-magnetic device has been disclosed, and in particular that a magnetic-permeable E-shield for the programming head of an implantable device programming system has been disclosed.

Although a specific embodiment of the invention has been disclosed herein in some detail, this has been done solely to illustrate various aspects of the invention and is not intended to be limiting with regard to the scope of the invention, which is believed to be advantageously applicable in devices other than implantable device programming heads. It is believed that various substitutions, alterations, and/or modifications, including but not limited to those design options specifically discussed herein, may be made to the disclosed embodiment of the invention without departing from the spirit and scope of the invention as defined in the appended claims, which follow. One alternative embodiment in particular is contemplated as being advantageously applied in situations not requiring magnetic permeability of the E-shield. In such applications, shielding may be accomplished by applying the conductive material to the entire inner surface of a device's exoskeleton.

What is claimed is:

1. A programming system for an implantable medical device, comprising:

a programmer base unit having a programming head cable extending therefrom;

a programming head, having a non-conductive structural exoskeleton and electrical components, said programming head being connected to said base unit by said programming head cable having a plurality of conductors therein for providing electrical connection between said head and said base unit and a patterned coating of conductive material applied to interior surfaces of said exoskeleton for providing shielding the interior of said exoskeleton from electric fields, said patterned coating electrically comprising areas which are electrically connected by a joining programming head electrical connector means connected also to said exoskeleton said connector means providing a conductive pathway to at least one of said conductors from said connected patterned coating areas.

2. A programming system in accordance with claim 1, wherein said conductive material is a nickel-acrylic paint.

3. A programming system in accordance with claim 1 wherein said patterned coating areas of conductive material are separated by an uncoated area along said interior surfaces of said exoskeleton so as to prevent any continuous flux paths within said patterned areas from surrounding said head.

4. A system as set forth in claim 3 wherein said uncoated area comprises a separating space on the interior of said exoskeleton between patterned areas of substantially 0.1 inches.

5. A programming system in accordance with claim 1, wherein said conductive material is coupled to at least one conductor in said programming head cable.

6. A programming system in accordance with claim 1, further comprising a strain relief collar extending through said exoskeleton and surrounding said programming head cable to provide strain relief for said programming head cable as it enters said exoskeleton.

7. A programming system in accordance with claim 6, wherein said strain relief collar is made at least partially of conductive material held in electrical contact with said areas of conductive material by means of said programming head connector means.

8. A programming system in accordance with claim 7, wherein said strain relief collar is also in electrical contact with and at least one conductor in said programming head cable.

9. An electric field shielding system for an electromagnetic apparatus having a non-conductive exoskeleton, said shielding system comprising:

a system base unit having a cable extending therefrom;

a system head having electrical components, said system head being electrically coupled to said base system by said cable having at least one conductor therein; and a plurality of isolated pattern areas of conductive material applied to interior surfaces of said exoskeleton for providing shielding of electric fields within said exoskeleton, said isolated pattern areas electrically coupled by a joining system head electrical connector means having a socket means adapted and disposed to be in close proximity therewith, said socket means providing a conductive pathway between said cable and said electrical components in said head.

10. A system in accordance with claim 9, wherein said plurality of isolated pattern areas of conductive material have a separation therein such that said electrical-field shield is magnetic-field permaeable.

11. A system in accordance with claim 9, further comprising a cable having at least one conductor, extending from an electrical ground terminal external to said exoskeleton, through said exoskeleton to a contact point on said pattern of conductive material, such that said pattern of conductive material is electrically grounded, wherein said conductive material is coupled to said at least one conductor in said cable.

12. A system in accordance with claim 9, further comprising a strain relief collar extending through said exoskeleton and surrounding cable to provide strain relief for said cable as it enters said exoskeleton.

13. A system in accordance with claim 12, wherein said strain relief collar is made at least partially of conductive material held in electrical contact with said pattern of conductive material.

14. A system in accordance with claim 13, wherein said strain relief collar is also in electrical contact with said at least one conductor in said programming head cable.

15. A programming system for an implantable medical device, comprising:

a programmer base unit having a programming head cable extending therefrom;

a programming head having a non-conductive exoskeleton and internal electrical components, said programming head being connected to said base unit by said programming head cable, said cable having a plurality of conductors therein; and a patterning of conductive material applied to interior surfaces of said exoskeleton for providing shielding from electric fields within said exoskeleton said patterning forming a single shield electrically connected by a joining programming head electrical connector means said connector means connecting said shield to a conductor in said cable and said head exoskeleton also having provided therein a socket means for providing a conductive pathway between said calbe and said internal electrical components.

* * * * *

UNITED STATES PATENT AND TRADEMARK OFFICE
CERTIFICATE OF CORRECTION

PATENT NO. : 5,527,348
DATED : June 18, 1996
INVENTOR(S) : Thomas J. Winkler, et. al.

It is certified that error appears in the above-identified patent and that said Letters Patent is hereby corrected as shown below:

Column 1, line 42 "signals-to" to be changed to "signals to"--
Column 7, line 58 "head," to be changed to "head"--
Column 8, line 55 "permaeable" to be changed to "permeable"--
Column 10, line 12, "calbe" tp be changed to "cable"--

Signed and Sealed this

Thirtieth Day of November, 1999

Attest:

Q. TODD DICKINSON

Attesting Officer

Acting Commissioner of Patents and Trademarks